United States Patent
Mueller et al.

(10) Patent No.: US 6,868,714 B2
(45) Date of Patent: Mar. 22, 2005

(54) VIBRATION SENSOR FOR FIXING DIRECTLY OR INDIRECTLY TO A VIBRATING COMPONENT

(75) Inventors: Wolfgang-Michael Mueller, Rutesheim (DE); Wolfgang Schmidt, Vaihingen (DE); Hartmut Brammer, Vaihingen (DE)

(73) Assignee: Robert Bosch GmbH, Stuttgart (DE)

( * ) Notice: Subject to any disclaimer, the term of this patent is extended or adjusted under 35 U.S.C. 154(b) by 117 days.

(21) Appl. No.: 10/129,830

(22) PCT Filed: Aug. 30, 2001

(86) PCT No.: PCT/DE01/03305

§ 371 (c)(1),
(2), (4) Date: Sep. 18, 2002

(87) PCT Pub. No.: WO02/21093

PCT Pub. Date: Mar. 14, 2002

(65) Prior Publication Data

US 2003/0056594 A1 Mar. 27, 2003

(30) Foreign Application Priority Data

Sep. 8, 2000 (DE) .......................................... 100 44 476

(51) Int. Cl.[7] .............................................. G01L 23/22
(52) U.S. Cl. ......................... 73/35.11; 73/654; 310/329
(58) Field of Search ............................. 73/35.11, 35.09, 73/649, 654, 652; 310/329

(56) References Cited

U.S. PATENT DOCUMENTS 5,474,616 A    12/1995  Hayami et al.
5,798,453 A  *  8/1998  Brammer et al. .......... 73/35.09
5,872,307 A  *  2/1999  Brammer et al. .......... 73/35.11
6,212,940 B1 *  4/2001  Castaing et al. ........... 73/35.11
6,220,078 B1 *  4/2001  Brammer et al. .......... 73/35.11
6,247,351 B1 *  6/2001  Brammer et al. .......... 73/35.11
2001/0020384 A1 * 9/2001 Mueller et al. ............ 73/35.11
2003/0005911 A1 * 1/2003 Subramanian et al. ..... 73/35.11

FOREIGN PATENT DOCUMENTS

| DE | 195 24 152 | 5/1996 |
| DE | 195 24 147 | 1/1997 |
| DE | 196 12 541 | 10/1997 |
| DE | 198 29 379 | 1/2000 |
| EP | 0184666 | 6/1986 |
| JP | 10267748 | 10/1998 |
| JP | 2000249598 | 9/2000 |

\* cited by examiner

*Primary Examiner*—Hezron Williams
*Assistant Examiner*—Nashmiya Fayyaz
(74) *Attorney, Agent, or Firm*—Kenyon & Kenyon

(57) ABSTRACT

A vibration sensor for direct or indirect mounting on a vibrating component has a housing, a pressure sleeve having a central bore and a piezoelectric disk situated between two insulator disks and two contact disks, a seismic mass acting on the disks by way of a spring element. The spring element is designed with a ring shape and has a projection on its inside ring area. On the outside circumference of the pressure sleeve there is a recess which is designed to correspond to the projection and is formed to accommodate the projection on the spring element.

14 Claims, 2 Drawing Sheets

VIBRATION SENSOR FOR FIXING DIRECTLY OR INDIRECTLY TO A VIBRATING COMPONENT

BACKGROUND INFORMATION

Vibration sensors are used, for example, as knock sensors in internal combustion engines. European Patent No. 0 184 666, for example, describes such a knock sensor, which is diagramed in FIG. 4. The knock sensor has a housing 2 and a pressure sleeve 3 on whose outside are arranged a piezoceramic disk 4 and a seismic mass 5 acting on it. Seismic mass 5 acts on piezoceramic disk 4 by way of a plate spring 6. The prestress on plate spring 6 is produced by a threaded ring 7 screwed onto the pressure sleeve. Pressure sleeve 3 therefore has an outside thread 8. The force applied to piezoceramic disk 4 may therefore be adjusted and limited as desired. Piezoceramic disk 4 is situated between two contact disks 9, these contact disks 9 being connected to a cable 11 by wires 10.

The arrangement described above for holding together the individual parts of the knock sensor by way of the threaded ring and the plate spring has the disadvantages that it is relatively expensive to manufacture and can also lead to manufacturing defects. In particular in the manufacture of outside thread 8 on pressure sleeve 3, shavings from cutting the thread, for example, may fall into the interspace between pressure sleeve 3 and piezoceramic element 4 when screwing on threaded ring 8. Therefore, a short circuit may occur after the sheathing has been extruded onto housing 2.

In addition, European Patent No. 0 184 666 describes the fastening of plate springs 6 by using a Seeger ring.

In addition, German Patent No. 195 24 152 describes a vibration sensor which has on the outside of the pressure sleeve bulges which function as a stop for the plate spring. These bulges are produced by caulking of the material of the pressure sleeve. However, inaccuracies in the prestress of the piezoceramic disk over the plate spring may occur here due to uneven caulking.

SUMMARY OF THE INVENTION

The vibration sensor according to the present invention for direct or indirect mounting on a vibrating component has the advantage over the related art that the ring-shaped spring element has a projection on its inside ring area, and a recess in the pressure sleeve which corresponds to the projection is formed on the outside of the pressure sleeve. In the installed state, the recess accommodates the projection on the spring element. Therefore, the spring element is held securely by its projection in the recess in the pressure sleeve and may thus exert a uniform prestressing force on a seismic mass or a piezoelectric disk. In addition, this also makes is possible to eliminate the threaded ring for prestressing the spring element or other parts which are used as a stop for the spring element. In addition, it is also unnecessary to cut an outside thread in the pressure sleeve. Instead, according to the present invention, a recess may be produced easily according to the present invention by lathing, for example. This makes production of the vibration sensor according to the present invention especially inexpensive. Furthermore, there is no risk of any shavings falling into the interspace between the piezoelectric disk and the pressure sleeve, which might result in a short circuit.

The spring element and the seismic mass are preferably designed in one piece, i.e., as one part. Due to the fact that only a single component is provided, this makes it possible firstly to reduce the number of parts and secondly to greatly simplify assembly and shorten assembly times. Since the spring element and the seismic mass are designed in one piece, the seismic mass is made of the same material as the spring element. A spring steel or the like may be used here, for example.

In order for the seismic mass or the one-piece part in the finished installed state to have the flattest possible contact surface with the insulator disks or contact disks, which are situated between the seismic mass or the one-piece part and the piezoelectric disk, the seismic mass or the one-piece part is designed with a conical taper in the relaxed state on the side facing the piezoelectric disk. In the installed state, this side is in flat contact; in other words, the seismic mass or the one-piece part bends like a plate spring which is pressed flatly on "block."

The projection preferably has at least one inclined surface. Therefore, the projection may be designed so that it has a wedge shape. This makes it possible to use larger component tolerances than in the related art for all the individual parts forming the vibration sensor. This has a very positive effect on manufacturing costs. Due to the design of the projection having at least one inclined surface, the bond is self-stressing in the axial direction of the vibration sensor.

The projection preferably has two inclined surfaces. Therefore, the projection may be designed so that it forms a tip which may engage in a corresponding recess having a V-shaped cross section in the pressure sleeve.

To be able to exert a sufficient prestressing force on the piezoelectric disk, the projection of the spring element preferably has a wedge-shaped tip having an angle of approximately 15° to approximately 120°. This reliably prevents the projection on the plate spring from falling out of the recess in the outside wall of the pressure sleeve. It is especially preferable for the angle here to be approximately 60°.

To provide additional security for the plate spring on the pressure sleeve, the spring element is additionally mounted on the pressure sleeve by welding. The plate spring is thus secured on the pressure sleeve by a welded joint, which may be produced by a laser welding method or a resistance welding method, for example. In welding the plate spring to the pressure sleeve, it is also possible to further prestress the plate spring by a radial and an axial force component.

Preferably a continuous slot is formed in the spring element and in the seismic mass. In the installed state of the individual parts of the vibration sensor, this slot has the function of providing a flow channel for the plastic of the housing, so that the plastic may also reach the inside area between the pressure sleeve and the seismic mass or the piezoelectric disk with no problem. To facilitate easy threading and thus rapid assembly of the seismic mass and the plate spring, a spacer is preferably provided in the slot before assembly to widen the parts so that they can easily be pushed onto the pressure sleeve.

In addition, at least one groove is preferably formed in the side of the spring element facing away from the piezoelectric disk. This groove also functions as a flow channel for plastic, and any desired number of grooves may be provided. In particular, the grooves must be present if there is no continuous slot in the spring element.

Thus, a vibration sensor made available according to the present invention is inexpensive to manufacture and easy to assemble, a projection being provided on the spring element to engage in a recess formed on the outside of the pressure sleeve. Therefore, the projection on the spring element may engage in the recess and thus be held in position.

DETAILED DESCRIPTION

Figure 1:
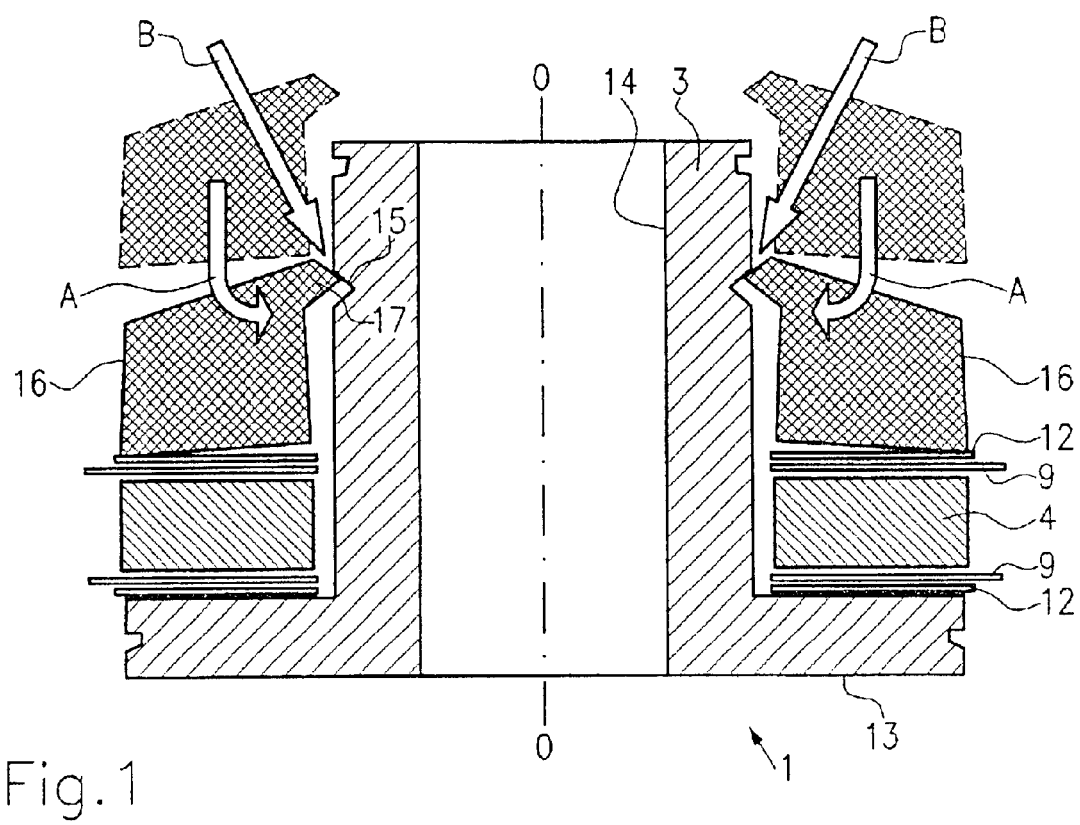
FIG. 1 shows a schematic side view of a vibration sensor according to a first embodiment of the present invention.
Figure 2:
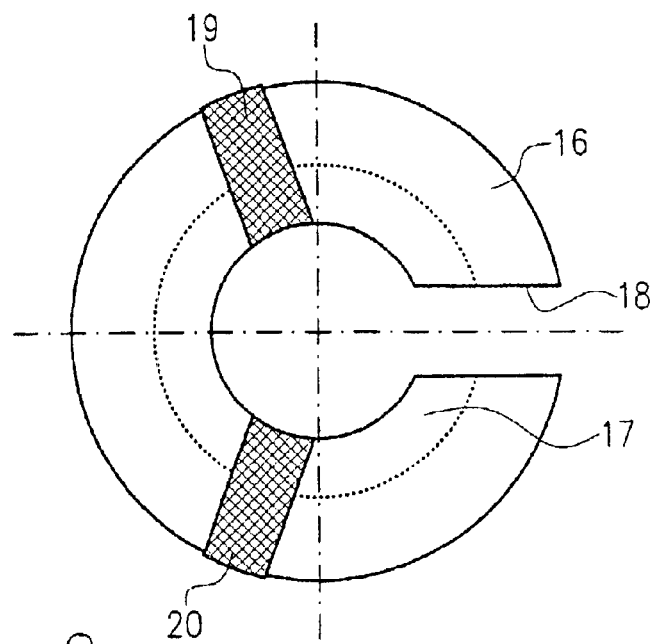
FIG. 2 shows a top view of the plate spring illustrated in FIG. 1.

FIGS. 1 and 2 show a vibration sensor according to the present invention for direct or indirect mounting on a vibrating component (not shown) according to a first embodiment of the present invention.

As shown in FIG. 1, vibration sensor 1 according to the present invention has a pressure sleeve 3 which has a flange-like edge on its lower end, forming a contact surface 13 on the side facing the vibrating component. In addition, pressure sleeve 3 has a central bore 14 which accommodates a fastening means for fastening the vibrating sensor onto the vibrating part.

In addition, as illustrated in FIG. 1, the pressure sleeve has a recess 15 having a V-shaped cross section on its outside, the recess being formed on the entire outer circumference of pressure sleeve 3.

In addition, the vibration sensor according to the first embodiment has a one-piece component 16 which functions as a seismic mass and as a spring element for applying prestress to piezoelectric disk 4 at the same time. As illustrated in FIG. 1, component 16 includes a wedge-shaped projection 17 which is formed on the upper inside peripheral ring of component 16. Wedge-shaped projection 17 engages in recess 15 formed in pressure sleeve 3. FIG. 1 shows component 16 before assembly with dotted lines and just prior to the final installed position with solid lines. Component 16 moves here in the direction of arrow A into the final assembly position. In the final position, the inclined surfaces of projection 17 are in direct contact with the inclined surfaces of recess 15. Therefore, recess 15 functions as a stop for projection 17 and thus determines the prestress acting on piezoelectric disk 4. In the final installed position, the bottom side of one-piece component 16 lies flat on insulator disk 12.

As illustrated in FIG. 1, component 16 acts on piezoelectric disk 4 by way of an insulator disk 12 and a contact disk 9. Piezoelectric disk 4 is in turn arranged in contact with the flange-like projection on pressure sleeve 3 by way of a contact disk 9 and an insulator disk 12.

FIG. 2 shows a top view of component 16 which forms the spring element and the seismic mass. As shown in FIG. 2, a continuous slot 18 is provided in component 16. Therefore, projection 17 is not completely ring shaped. In addition, two grooves 19 and 20 are provided in the upper area of component 16. These grooves function as flow channels for a plastic which is molded around the preassembled individual parts as a housing (not shown) after preassembly of the individual parts, so that plastic can also reach between component 16 and piezoelectric disk 4 and the cylindrical area of pressure sleeve 3. Slot 18 also has the same function as grooves 19 and 20, forming a broad passage for the injection molding plastic. In addition, slot 18 simplifies placement of component 16 over pressure sleeve 3, because component 16 can then be widened easily and easily pushed over pressure sleeve 3. A spacer is preferably arranged in slot 18 before assembly to hold component 16 in the widened state.

Figure 3:
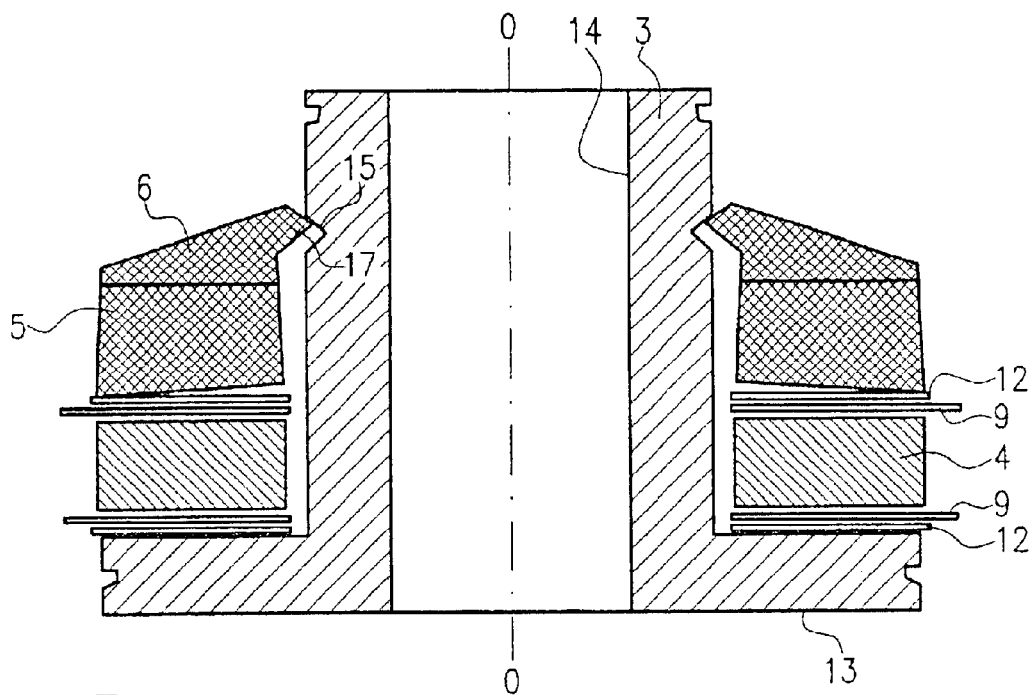
FIG. 3 shows a schematic sectional view of a vibration sensor according to a second embodiment of the present invention.
Figure 4:
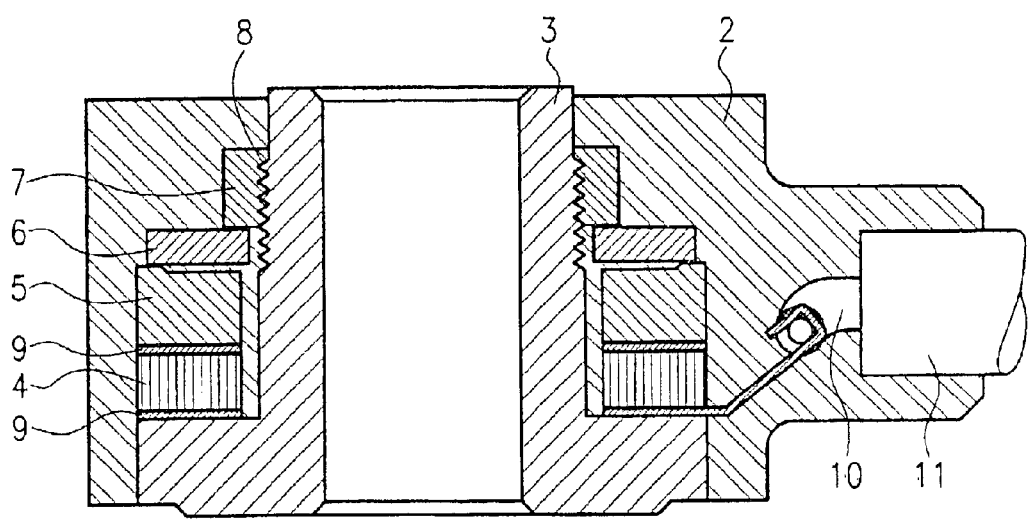
FIG. 4 shows a side view of a vibration sensor according to the related art.

FIG. 3 shows a second embodiment according to the present invention. The same or similar parts are designated with the same reference notation as in the first embodiment and are therefore not described in detail below.

In contrast with the first embodiment, a one-piece component is no longer provided for the seismic mass and the plate spring in the second embodiment, but instead two separate components are provided, namely a seismic mass 5 and a plate spring 6. As shown in FIG. 3, seismic mass 5 is designed as a ring-shaped disk in the known manner. On its inside circumferential area, plate spring 6 has a projection 17 shaped like a wedge. As shown in FIG. 3, projection 17 has two inclined surfaces which in the installed state engage in a V-shaped recess 15 on the outside of pressure sleeve 3. Therefore, plate spring 6 exerts a prestress on seismic mass 5 and piezoelectric disk 4. The additional components of the vibration sensor according to the second embodiment correspond to those in the first embodiment and therefore will not be described in detail below.

In addition, it is possible with both embodiments for component 16 or plate spring 6 to additionally be mounted on pressure sleeve 3 by a weld to increase the long-term stability of the vibration sensor. This is indicated with arrows B in FIG. 1. In addition, it is also possible in the welding operation for an additional prestress to be applied to component 16 or spring element 6 by a radial force component and an axial force component.

In summary, the present invention relates to a vibration sensor for direct or indirect mounting on a vibrating component, having a housing, a pressure sleeve 3 with a central bore 14 and a piezoelectric disk 4 situated between two insulator disks 12 and two contact disks 9 on which a seismic mass 5 acts by way of a spring element 6. Spring element 6 is designed with a ring shape and has a projection 17 on its inside ring area. A recess 15 which is designed to match the projection is formed on the outside circumference of pressure sleeve 3 to receive projection 17 of spring element 6.

The previous description of the embodiments according to the present invention is given only for illustrative purposes and not for the purpose of restricting the scope of the present invention. Various changes and modifications are possible within the scope of the present invention without going beyond the scope of the present invention or its equivalents.

What is claimed is:

1. A vibration sensor for direct or indirect mounting on a vibrating component, comprising:
    a pressure sleeve having a central bore and an outside circumference;
    two insulator disks;
    two contact disks;
    a piezoelectric disk situated between the two insulator disks and the two contact disks;
    a spring element having a ring shape and an inside ring area, the spring element further having a single annular projection integrally projecting the inside ring area; and
    a seismic mass acting on each of the disks via the spring element,
    wherein an annular recess corresponding to the projection is situated on the outside circumference of the pressure sleeve to accommodate the projection on the spring element.

2. The vibration sensor according to claim 1, wherein the spring element and the seismic mass are designed as a one-piece part.

3. The vibration sensor according to claim 1, wherein the seismic mass has a conical taper in a relaxed state on a side facing the piezoelectric disk.

4. The vibration sensor according to claim 1, wherein the projection has at least one inclined surface.

5. The vibration sensor according to claim 1, wherein the projection has two inclined surfaces.

6. The vibration sensor according to claim 1, wherein the projection has a wedge-shaped tip having an angle of about 15° to 120°.

7. A vibration sensor for direct or indirect mounting on a vibrating component, comprising:

a pressure sleeve having a central bore and an outside circumference;

two insulator disks;

two contact disks;

a piezoelectric disk situated between the two insulator disks and the two contact disks;

a spring element having a ring shape and an inside ring area, the spring element further having a projection on the inside ring area;

a seismic mass acting on each of the disks via the spring element, and a continuous slot in the ring shape of the spring element and the seismic mass, wherein a recess corresponding to the projection is situated on the outside circumference of the pressure sleeve to accommodate the projection on the spring element.

8. A vibration sensor for direct or indirect mounting on a vibrating component, comprising:

a pressure sleeve having a central bore and an outside circumference;

two insulator disks;

two contact disks;

a piezoelectric disk situated between the two insulator disks and the two contact disks;

a spring element having a ring shape and an inside ring area, the spring element further having a projection on the inside ring area;

a seismic mass acting on each of the disks via the spring element;

wherein a recess corresponding to the projection is situated on the outside circumference of the pressure sleeve to accommodate the projection on the spring element, wherein the spring element and the seismic mass are designed as a one-piece part; and a continuous slot in the ring shape of the one-piece part.

9. The vibration sensor according to claim 1, further comprising at least one groove situated in a side of the spring element facing away from the piezoelectric disk, the groove being formed from an outside circumference to an inside circumference.

10. The vibration sensor according to claim 7, further comprising a spacer situated in the slot for providing a simple sliding onto the pressure sleeve.

11. The vibration sensor according to claim 1, wherein the projection is additionally fastened on the pressure sleeve by welding.

12. The vibration sensor according to claim 1, wherein the recess and the projection are complementary.

13. The vibration sensor according to claim 1, wherein the recess is arranged as an annular groove around the outside circumference of the pressure sleeve.

14. The vibration sensor according to claim 1, wherein the recess is formed on the entire outside circumference of the pressure sleeve.

* * * * *